US012433525B2

(12) United States Patent
Slater et al.

(10) Patent No.: US 12,433,525 B2
(45) Date of Patent: Oct. 7, 2025

(54) ELECTRODE ARRAY ASSEMBLY

(71) Applicant: Seer Medical Pty Ltd, Melbourne (AU)

(72) Inventors: Kyle Damon Slater, Melbourne (AU); John Lloyd Grant, Melbourne (AU); Kate Hou, Melbourne (AU); Jaydan William Bloye, Melbourne (AU)

(73) Assignee: Seer Medical Pty Ltd, Melbourne (AU)

( * ) Notice: Subject to any disclaimer, the term of this patent is extended or adjusted under 35 U.S.C. 154(b) by 254 days.

(21) Appl. No.: 17/755,702

(22) PCT Filed: Nov. 6, 2020

(86) PCT No.: PCT/AU2020/051206
§ 371 (c)(1),
(2) Date: May 5, 2022

(87) PCT Pub. No.: WO2021/087565
PCT Pub. Date: May 14, 2021

(65) Prior Publication Data

US 2022/0386923 A1 Dec. 8, 2022

(30) Foreign Application Priority Data

Nov. 6, 2019 (AU) ................................ 2019904175

(51) Int. Cl.
*H01R 13/73* (2006.01)
*A61B 5/273* (2021.01)
(Continued)

(52) U.S. Cl.
CPC .............. *A61B 5/291* (2021.01); *A61B 5/273* (2021.01); *H01R 13/506* (2013.01); *H01R 13/6205* (2013.01); *A61B 2562/046* (2013.01)

(58) Field of Classification Search
CPC ... A61B 5/291; A61B 5/273; A61B 2562/046; H01R 13/506; H01R 13/6205
(Continued)

(56) References Cited

U.S. PATENT DOCUMENTS

| | | | | |
|---|---|---|---|---|
| 3,735,753 | A | 5/1973 | Pisarski | |
| 4,537,198 | A | 8/1985 | Corbett | |
| 6,356,778 | B1 * | 3/2002 | Pirc | A61B 5/273 439/852 |
| 6,394,953 | B1 | 5/2002 | Devlin et al. | |

(Continued)

FOREIGN PATENT DOCUMENTS

| | | |
|---|---|---|
| GB | 2075194 A | 11/1981 |
| WO | 199714358 A1 | 4/1997 |

OTHER PUBLICATIONS

International Search Report and Written Opinion in International Application No. PCT/AU2020/051206, mailed Feb. 3, 2021 (14 pages).

*Primary Examiner* — Harshad C Patel
(74) *Attorney, Agent, or Firm* — Bookoff McAndrews, PLLC

(57) ABSTRACT

Electrode array assembly (10) including a carrier assembly (12) and a connector assembly (14). The carrier assembly (12) includes an array of first electrical contacts (20) coupled to a plurality of electrodes (18), and a first housing (22) carrying the array of first contacts (20) and configured to allow access to the first contacts (20). The connector assembly (14) includes an array of second electrical contacts (26), and a second housing (28) carrying the second contacts (26) and configured to allow access to the second contacts (26). Each of the carrier assembly (12) and the connector assembly (14) include complementary retention elements (30) and complementary locating formations (32), whereby engaging the complementary locating formations (32) allows the complementary retention elements (30) to secure the first
(Continued)

housing (22) to the second housing (28), and allows the first contacts (20) to couple with the second contacts (26).

20 Claims, 7 Drawing Sheets

(51) Int. Cl.
*A61B 5/291* (2021.01)
*H01R 13/506* (2006.01)
*H01R 13/62* (2006.01)

(58) Field of Classification Search
USPC .......................................................... 439/894
See application file for complete search history.

(56) References Cited

U.S. PATENT DOCUMENTS

| | | | | |
|---|---|---|---|---|
| 6,554,649 | B2 * | 4/2003 | Pade | G01N 27/4071 439/620.17 |
| 7,214,107 | B2 * | 5/2007 | Powell | H01R 11/22 439/729 |
| 9,203,175 | B1 | 12/2015 | Osa | |
| 9,774,137 | B2 * | 9/2017 | Park | H01R 13/6683 |
| 10,297,950 | B2 * | 5/2019 | Wei | A41D 13/0051 |
| 10,322,060 | B2 * | 6/2019 | Fleischacker | G09B 23/288 |
| 10,758,732 | B1 * | 9/2020 | Heldman | A61N 1/37235 |
| 11,647,955 | B2 * | 5/2023 | Pacholik | A61B 5/274 600/391 |
| 2014/0275927 | A1 | 9/2014 | Simpson | |
| 2014/0303472 | A1 | 10/2014 | Callahan | |
| 2015/0073285 | A1 * | 3/2015 | Albert | A61B 5/28 600/509 |

* cited by examiner

ELECTRODE ARRAY ASSEMBLY

CROSS-REFERENCE TO RELATED APPLICATIONS

This application is the U.S. national phase entry under 35 U.S.C. § 371 of International Application No. PCT/AU2020/051206, filed on Nov. 6, 2020, which claims the benefit of priority of Australian Patent Application No. 2019904175, filed on Nov. 6, 2019, each of which is incorporated by reference herein in its entirety.

TECHNICAL FIELD

The present disclosure relates, generally, to electrode array assemblies for use with patients and, particularly, relates to an electroencephalogram (EEG) electrode assembly for monitoring brain activity of a patient.

BACKGROUND

Patients are often monitored using an electrode assembly, for example, to obtain electroencephalogram (EEG) or electrocardiogram (ECG) data. Monitoring brain activity using EEG recording is typically performed by coupling an array of electrodes to a patient's scalp. The electrodes are secured by either a dry connection or a conductive paste, gel or glue to lower the impedance to tissue. Electrical connection to each electrode is formed using a respective number of wires. The wires are bundled and connected to EEG measurement equipment. Such equipment may be static (referred to as bedside) or portable (referred to as ambulatory).

EEG electrode arrays require a cable bundle that is terminated at a plurality of single conductor connectors which connect to each electrode. The cable bundle is typically bulky and can be uncomfortable for the patient. Typical connector arrangements which connect to each electrode lead are also often large and uncomfortable.

For some patients, EEG recording requires multiple day (potentially week-long) ambulatory monitoring, which involves wearing an EEG electrode array continuously for this period. This is often inconvenient and can prove distressing for patients as wearing the EEG electrode array means that routine activities can be difficult or impossible, such as having a shower.

Any discussion of documents, acts, materials, devices, articles or the like which has been included in the present specification is not to be taken as an admission that any or all of these matters were common general knowledge in the field relevant to the present disclosure as it existed before the priority date of each of the appended claims.

SUMMARY

According to some disclosed embodiments, there is provided an electrode array assembly including: a carrier assembly including an array of first electrical contacts coupled to a plurality of electrodes, and a first housing carrying the array of first contacts and configured to allow access to the first contacts; and a connector assembly including an array of second electrical contacts and a second housing carrying the array of second contacts and configured to allow access to the second contacts. Each of the carrier assembly and the connector assembly include complementary retention elements and complementary locating formations, whereby engaging the complementary locating formations allows the complementary retention elements to secure the first housing to the second housing, and allows the first contacts to couple with the second contacts.

The locating formation of the carrier assembly may include at least one locating aperture defined by the first housing, and the locating formation of the connector assembly may include at least one locating protrusion defined by the second housing. The, or each, locating protrusion may be dimensioned to be at least partially received in the at least one locating aperture.

The first housing may define a plurality of the locating apertures arranged in a circular array around the first contacts, and the second housing may define a complementary plurality of the locating protrusions arranged in a circular array around the second contacts.

Each of the locating protrusions may define a tapered free end shaped to allow guiding the protrusion into one of the locating apertures.

The retention element of the carrier assembly may include at least one first magnetic element enclosed in the first housing, and the retention element of the carrier assembly may include at least one second magnetic element enclosed in the second housing. The, or each, second magnetic element may be arranged to be drawn towards the, or each, first magnetic element when the locating formations are engaged.

Each of the at least one first magnetic element and the at least one second magnetic element may be configured as a ring magnet and arranged to surround the respective contacts.

The first contacts may be configured as pads, and the second contacts may be configured as pins.

The first housing may define an array of contact apertures, each contact aperture arranged to allow access to one of the pads.

Each of the electrodes may be coupled to one of the first contacts by a wire, and the first housing may include a base plate defining a plurality of openings, each opening dimensioned to receive one of the wires.

The first housing may also include a cover securable to the base plate to retain the wires in the openings.

The cover may define a rib extending at least partially around a peripheral region, the rib arranged so that securing the cover to the base plate clamps the wires between the base plate and the rib.

According to other disclosed embodiments, there is provided an electrode array assembly including a plurality of electrodes coupled to a respective plurality of wires, a base plate configured to carry the plurality of electrodes and wires, and defining a plurality of openings, each opening dimensioned to receive one of the wires, and a first cover securable to the base plate to retain the wires in the openings.

The first cover may define a rib extending at least partially around a peripheral region, the rib arranged so that securing the first cover to the base plate clamps the wires between the base plate and the rib.

The assembly may also include an array of electrical contacts coupled to the plurality of electrodes, and a second cover securable to the base plate to cover the electrical contacts, the second cover defining a plurality of apertures configured to allow access to the electrical contacts.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated embodiments may comprise steps, features and/or integers disclosed herein or indicated in the specification of this application individually or collectively, and any and all combinations of two or more of said steps or features.

BRIEF DESCRIPTION OF DRAWINGS

Embodiments will now be described by way of example only with reference to the accompany drawings in which.

DESCRIPTION OF EMBODIMENTS

Figure 1:
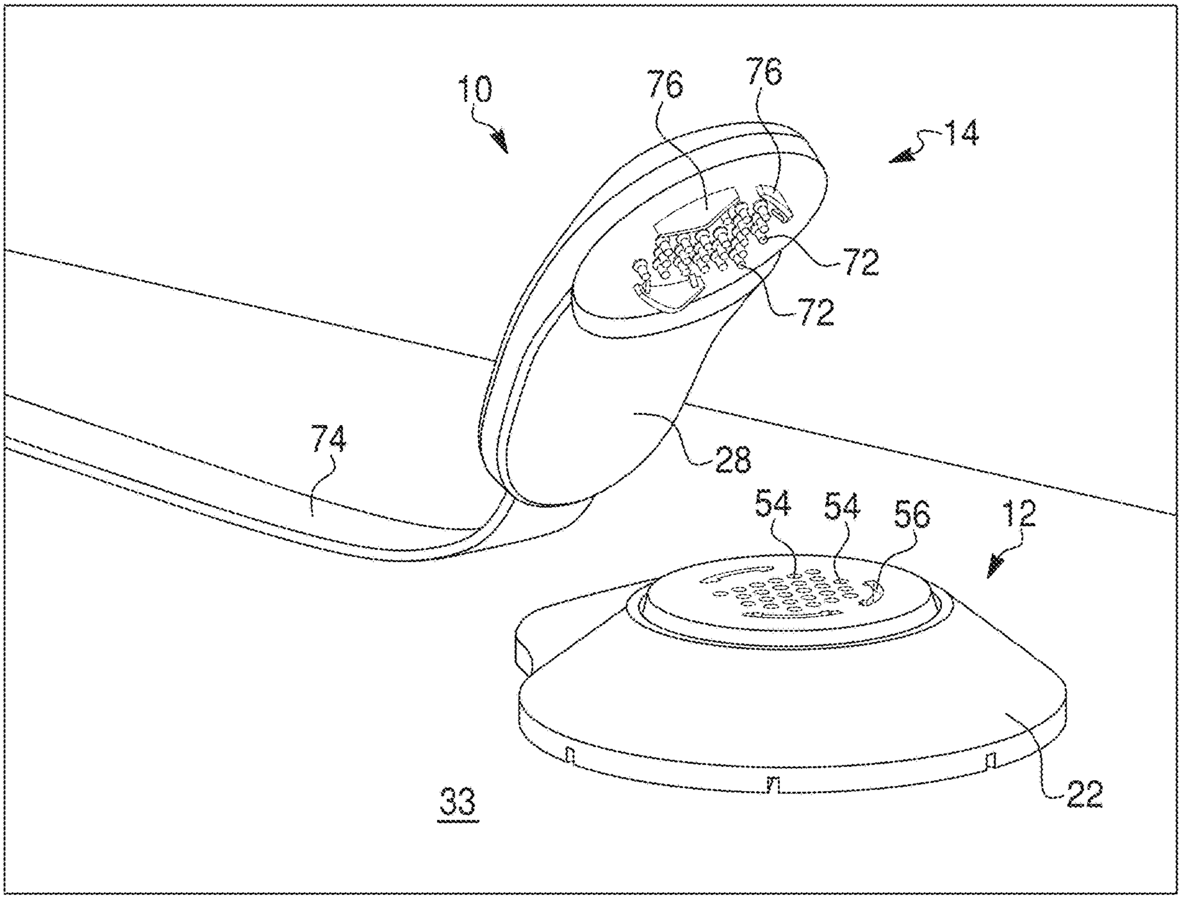
FIG. 1 is a perspective view of an electrode assembly including a carrier assembly and a connector assembly.

In the drawings, reference numeral 10 generally designates an electrode array assembly 10 including a carrier assembly 12 and a connector assembly 14. The carrier assembly 12 includes an array of first electrical contacts 20 coupled to a plurality of electrodes 18, and a first housing 22 carrying the array of first contacts 20 and configured to allow access to the first contacts 20. The connector assembly 14 includes an array of second electrical contacts 26, and a second housing 28 carrying the second contacts 26 and configured to allow access to the second contacts 26. Each of the carrier assembly 12 and the connector assembly 14 include complementary retention elements 30 and complementary locating formations 32, whereby engaging the complementary locating formations 32 allows the complementary retention elements 30 to secure the first housing 22 to the second housing 28, and allows the first contacts 20 to couple with the second contacts 26.

Throughout the specification the electrode array assembly 10 is described in relation to recording EEG data. However it will be appreciated that the electrodes 18 may be adapted to record alternative data, such as ECG data, and therefore the assembly 10 is suitable for other uses.

FIG. 1 shows the carrier assembly 12 arranged on a surface 33 and the connector assembly 14 disconnected from, and spaced above, the carrier assembly 12. The carrier assembly 12 is configured as a disposable arrangement which is wearable on a patient's body, typically being arranged on the scalp (not illustrated), or secured to a cap (not illustrated) worn on the scalp. The connector assembly 14 is configured as a re-usable (non-disposable) arrangement which is releasably connectable to the carrier assembly 12 to allow connecting monitoring equipment to the electrodes 18, for example, to record EEG data.

FIGS. 2 to 6 show the carrier assembly 12 in isolation, illustrating stages of assembling the carrier assembly 12 for use.

Figure 2:
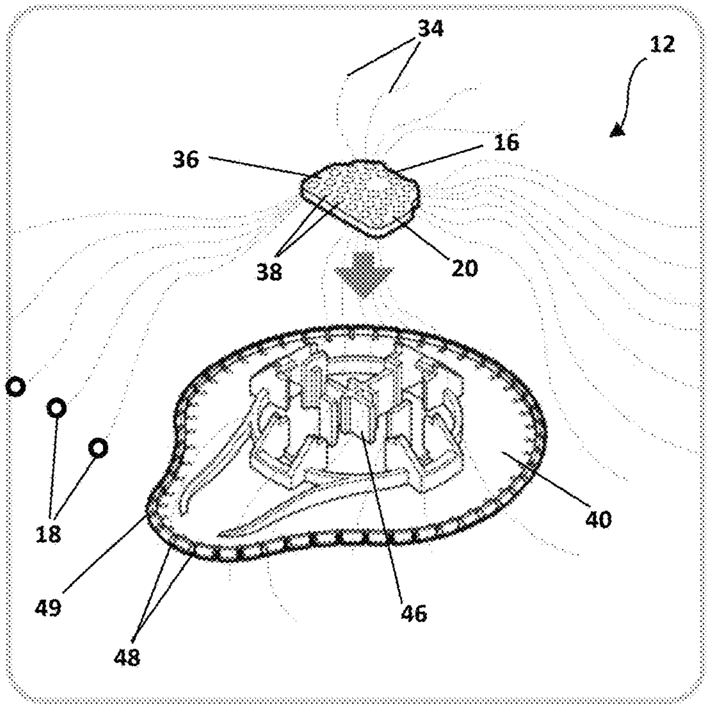
FIGS. 2 to 6 are perspective views of assembling the carrier assembly for use.
Figure 6:
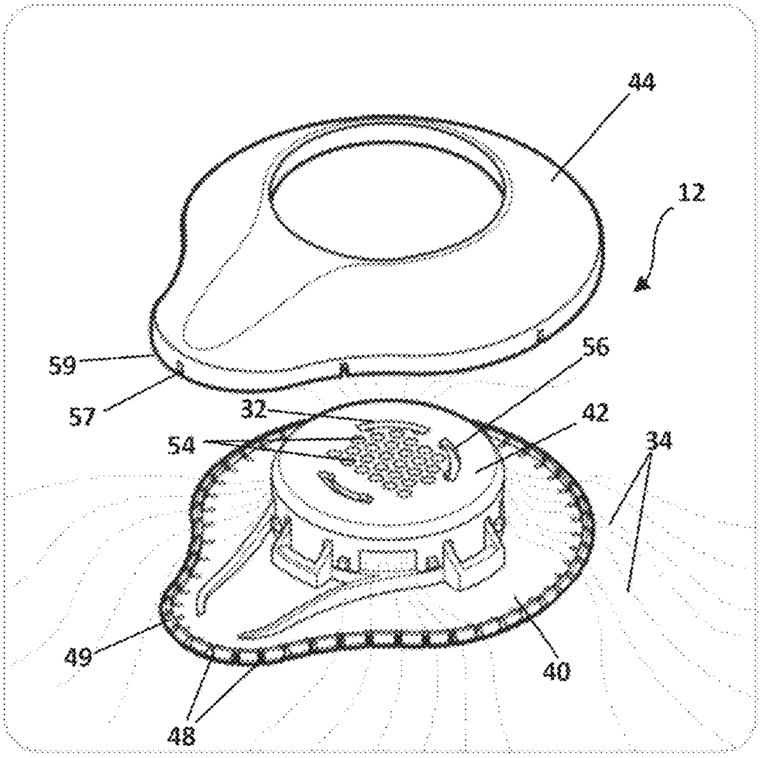

In FIG. 2, a first PCB 16 is shown spaced above the first housing 22 and connected to the electrodes 18 by a respective plurality of wires 34. A top surface 36 of the PCB 16 carries the array of first electrical contacts 20, in the form of pads 38. In the illustrated embodiment, the first housing 22 includes multiple, connectable bodies, being a base plate 40, an inner cover 42 (FIG. 4) and an outer cover 44 (FIG. 6).

In other embodiments (not shown), the first housing 22 is configured to comprise more or less bodies. For example, in some embodiments (not shown), the inner cover 42 and the outer cover 44 are integrally formed.

In other embodiments (not shown), the PCB 16 is absent from the carrier assembly 12 and instead the first contacts 20 are supported by the base plate 40 and directly coupled to the electrodes 18 via the wires 34. In some such embodiments (not shown), the ends of the wires 34 are arranged together and over-moulded so that the wires 34 are secured together by a moulded polymeric body. The contacts 20 are then coupled to the wires 34, for example, by conductive ink printed on the polymeric body. In yet other embodiments (not shown), the contacts 20 are coupled to the wires 34 prior to moulding to allow securing the contacts 20 in the polymeric body.

Figure 3:
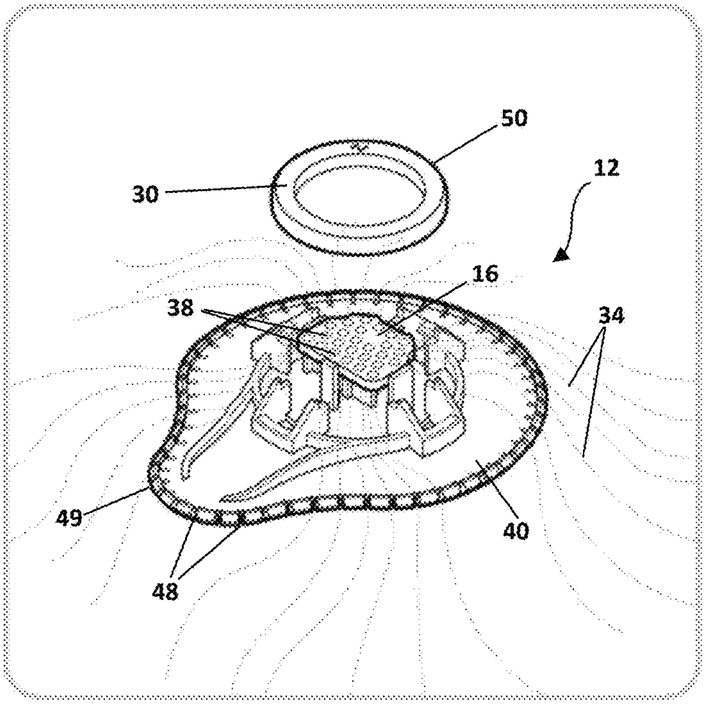

FIG. 3 shows the first PCB 16 supported on a mounting formation 46 defined by the base plate 40, and each of the wires 34 arranged in an opening 48 defined by the base plate 40. The openings 48 are configured as slots extending through a rim 49 of the base plate 40. Each opening 48 is dimensioned to receive, and typically dimensioned to also frictionally engage, one of the wires 34. One of the retention elements 30, in the form of a ring magnet 50, is shown spaced above the base plate 40. In other embodiments (not shown), the retention element 30 is configured as a plurality of button magnets securable to the base plate 40 to be disposed about the PCB 16.

Figure 4:
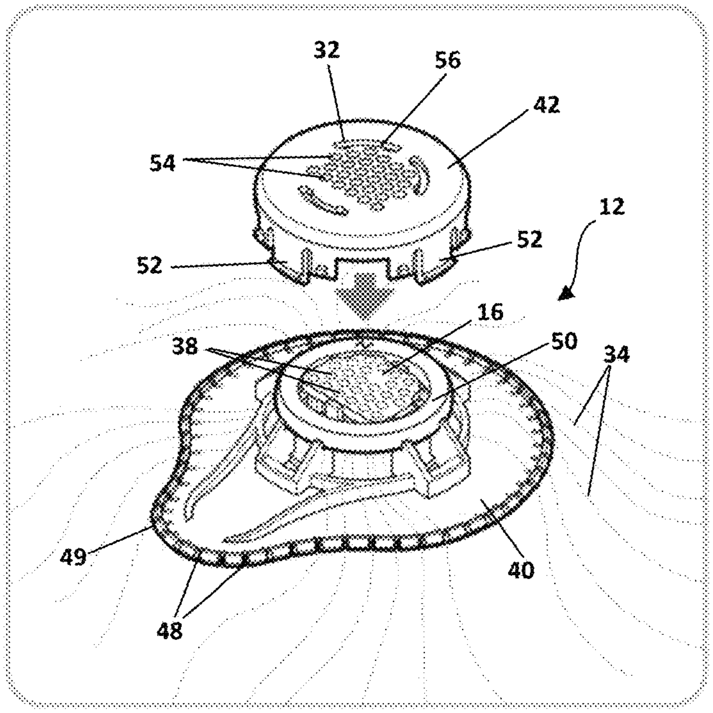

FIG. 4 shows the ring magnet 50 supported on the mounting formation 46 to surround the contact pads 38. The inner cover 42 is shown spaced above the mounting formation 46. The inner cover 42 has flexible snap-fit tabs 52 operable to engage the mounting formation 46 to secure the inner cover 42 to the base plate 40.

Figure 5:
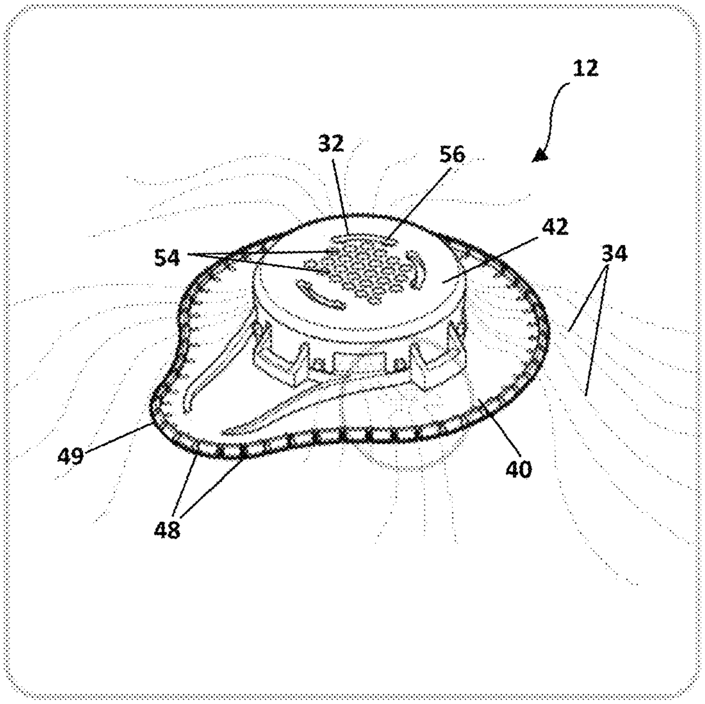

FIG. 5 shows the inner cover 42 secured to the base plate 40 to clamp the PCB 16 and ring magnet 50 to the mounting formation 46. The inner cover 42 defines a plurality of contact apertures 54. Each aperture 54 is arranged to allow access to one of the contact pads 38, and dimensioned to prevent a user's fingers from touching the pads 38. The inner cover 42 further defines one of the locating formations 32, in the form of a circular array of three locating apertures 56 surrounding the contact apertures 54 and the contact pads 38 arranged below. It will be appreciated that in other embodiments the inner cover 42 defines more or less locating apertures 56. For example, in some embodiments (not shown) the inner cover 42 defines a single, arcing slot substantially surrounding the contact apertures 54.

FIG. 6 shows the outer cover 44 spaced above the base plate 40. The outer cover 44 is securable to the base plate 40 to retain the wires 34 in the openings 48. The outer cover includes slots 57 extending through a sidewall 59 to divide the sidewall into sections. The sections are resiliently deformable and shaped to allow the outer cover 44 to engage the rim 49 of the base plate 40.

Figure 7:
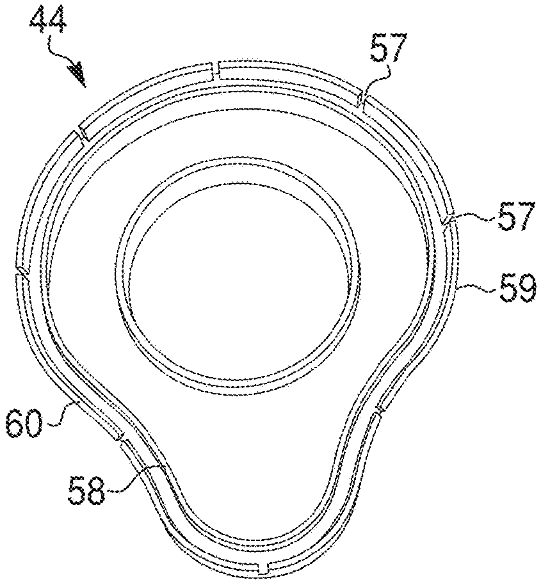
FIGS. 7 and 8 are plan and perspective views, respectively, of an outer cover which is part of the carrier assembly shown in FIGS. 2 to 6.
Figure 8:
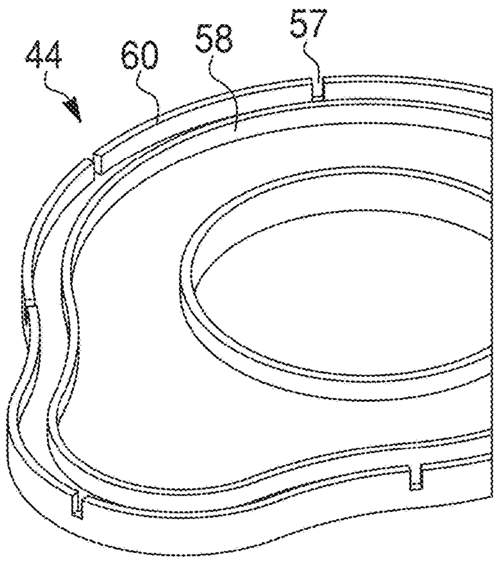

FIGS. 7 and 8 show the outer cover 44 in more detail, illustrating an underside of the cover 44. The outer cover 44 defines a rib 58 extending at least partially around a peripheral region of the cover 44. In the embodiment shown, the rib 58 is continuous around the peripheral region. In other embodiments (not illustrated), the cover 44 defines multiple, separate ribs. The rib 58 is spaced inwardly of a rim 60 of the cover 44. When the cover 44 is secured to the base plate 40, the rib 58 is urged against the wires 34 to clamp the wires 34 between the base plate 40 and the rib 58.

Figure 9:
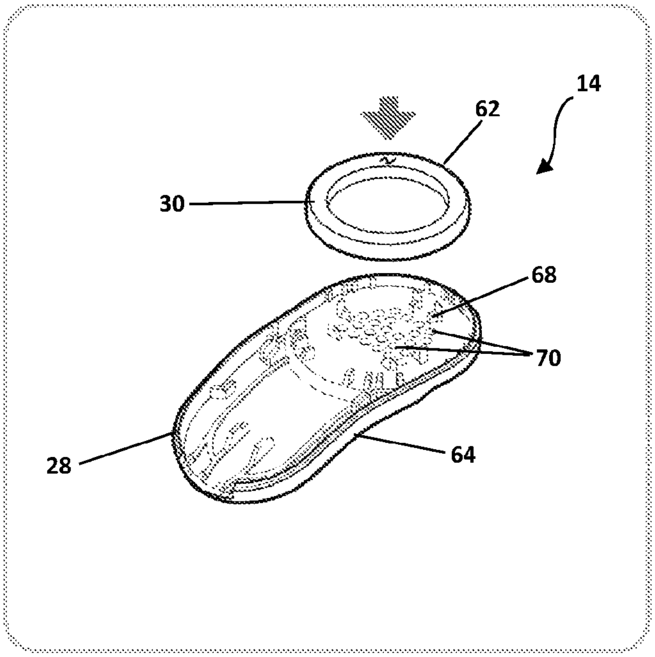
FIGS. 9 to 11 are perspective views of assembling the connector assembly for use.
Figure 10:
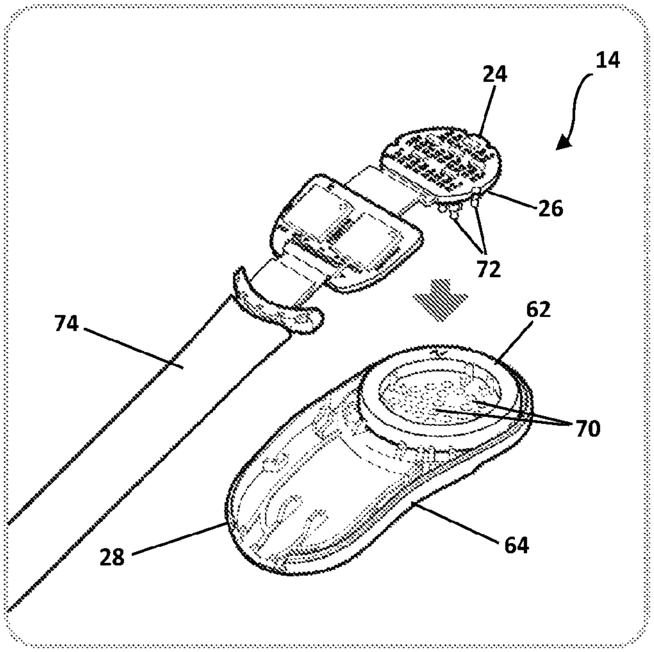
Figure 11:
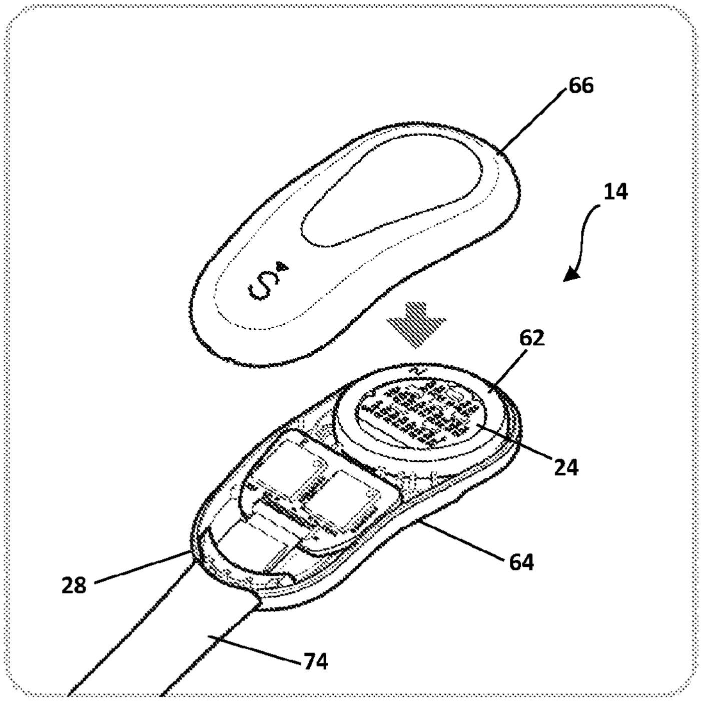

FIGS. 9 to 11 show the connector assembly 14 in isolation, illustrating stages of assembling the connector assembly 14 for use.

In FIG. 9, another retention element 30, in the form of a ring magnet 62, is shown spaced above the second housing 28. The second housing 28 includes a pair of connectable bodies, being a lower body 64 and an upper body 66 (FIG. 11). The lower body 64 defines a mounting formation 68 arranged to support the ring magnet 62. The lower body 64 further defines an array of contact apertures 70. Each of the apertures 70 are dimensioned to receive one of the second contacts 26, in the form of contact pins 72 (FIG. 10).

FIG. 10 shows the ring magnet 62 supported by the mounting formation 68 and a second PCB 24 spaced above the lower body 64 and connected to a ribbon cable 74. The second PCB 24 carries the contact pins 72, typically configured as depressible 'pogo' pins. In other embodiments (not shown), the PCB 24 is absent and instead, the contacts pins 72 are directly mounted to the lower body 64 and coupled to the ribbon cable 74.

FIG. 11 shows the second PCB 24 supported by the mounting formation 68 such that the ring magnet 62 surrounds the PCB 24 and the contact pins 72. The upper body 66 is shown spaced above the lower body 64. The upper body 66 includes deformable clip features (not shown) to allow the upper body 66 to be secured to the lower body 64 to clamp the PCB 24, magnet 62 and ribbon cable 74 between the bodies 64, 66.

Best shown in FIG. 1, when the PCB 24 is supported on the mounting formation 68, the contact pins 72 extend through the contact apertures 70 to protrude from a side of the lower body 64.

Also best shown in FIG. 1, the upper body 66 defines one of the locating formations 32, in the form of a circular array of three locating protrusions 76. Each protrusion 76 is dimensioned to be at least partially received in one of the locating apertures 56. The array of locating protrusions 76 is arranged to be complementary to the array of locating apertures 56 so that each protrusion 76 can engage a corresponding aperture 56. Each protrusion 76 defines a free end 78 which is tapered to assist guiding the protrusion 76 into one of the apertures 56.

FIGS. 12 to 16 show cross-section views to illustrate stages of engaging one of the locating protrusions 76 with one of the locating apertures 56.

Figure 12:
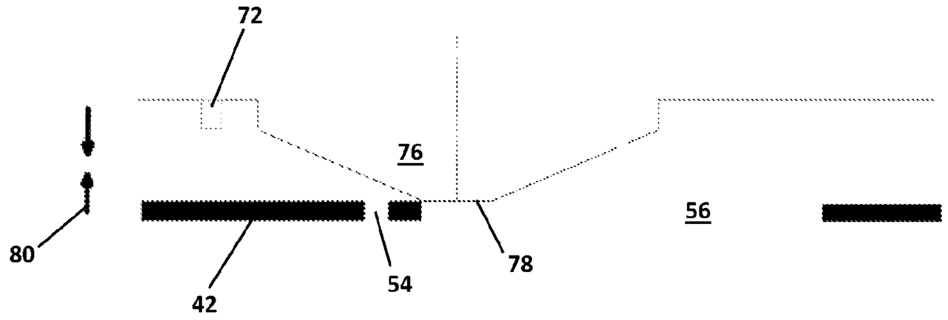
FIGS. 12 to 15 are cross-section detailed views showing the connector assembly engaging the carrier assembly.
Figure 13:
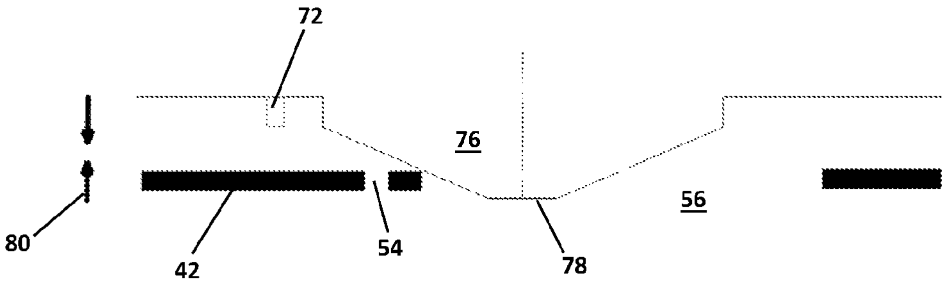
Figure 14:
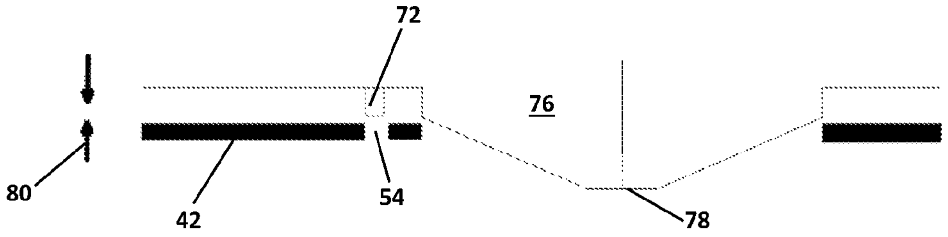
Figure 15:
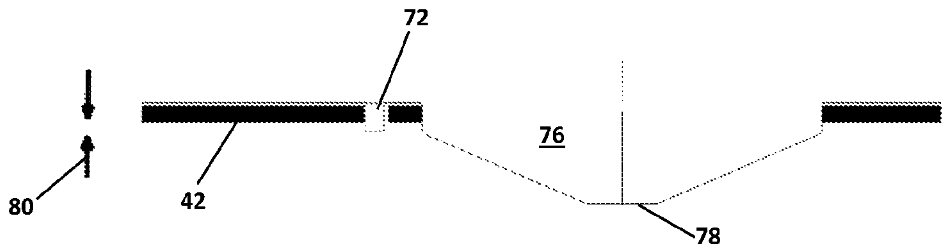

In FIG. 12, the free end 78 of the locating protrusion 76 is shown colliding with a top surface of the inner cover 42. In FIG. 13, the protrusion 76 is shown slightly rotated relative to the cover 43 so that the tapered free end 78 slides along a rim of the locating aperture 56 to guide the protrusion 76 into the aperture 56. This movement is assisted by the ring magnets 50, 62 being drawn towards each other by magnetic attraction (indicated by arrows 80). FIG. 14 shows the protrusion 76 further rotated relative to the cover 43 to be aligned with the aperture 56. FIG. 15 shows the protrusion 76 engaged with the aperture 56 also causing one of the contact pins 72 to pass through one of the contact apertures 54.

It will be appreciated that whilst the complementary locating formations 32 are shown in the illustrated embodiments as locating protrusions 76 and locating apertures 56, these formations 32 may be alternatively configured to provide suitable engagement between the carrier assembly 12 and the connector assembly 14. Similarly, whilst the complementary retention elements 30 are shown in the illustrate embodiments as ring magnets 50, 62, the retention elements 30 may be alternative configured to suitably secure the assemblies 12, 14 together. For example, in some embodiments (not shown) the locating formations 32 and retention elements 30 are combined together as a bayonet-type fitting. In other embodiments (not shown), the retention elements 30 are configured as resiliently deformable clip features specified to firmly secure the assemblies 12, 14 together to resist separation during vigorous activity, for example, should the patient experience a seizure.

The assembly 10 is typically provided to clinicians assembled as shown in FIG. 5, i.e. with the inner cover 42 secured to the base plate 40 to enclose the first PCB and the contact pads 36. This is to ensure clinicians and patients are unable to touch the pads 36.

Use of the assembly 10 involves a clinician securing the electrodes 18 in appropriate locations on the patient's scalp and placing the baseplate 40 on the scalp. Optionally, the clinician may adhere the baseplate 40 in place with an adhesive. The wires 34 are then drawn taught by the clinician withdrawing slack wire 34 onto the baseplate 40 (as shown in FIG. 5) and engaging each wire 34 with one of the openings 48. The outer cover 44 is secured to the base plate 40 to trap the wires 34 between the cover 44 and the base plate 40 so that the taught wires 34 retain the baseplate 40 against the scalp. This completes fitting and assembly of the carrier assembly 12.

The connector assembly 14 is placed in contact with the carrier assembly 12 so that the locating protrusions 76 are substantially aligned with the locating apertures 56. The connector assembly 14 is moved relative to the carrier assembly 12 until the tapered free ends 78 of the protrusions 76 guide engagement with the apertures 56. This is assisted by the ring magnets 56, 62 drawing the connector assembly 14 and carrier assembly 12 towards each other, particularly due to the self-aligning characteristics of the ring magnets 56, 62 whereby the force of magnetic attraction is strongest at a central axis causing the magnets 56, 62 to align. When the locating protrusions 76 are seated in the locating apertures 56 the contact pins 72 extend through the contact apertures 54 defined in the inner cover 42 to abut the contact pads 38 and form an electrical connection between the assemblies 12, 14. The ribbon cable 74 is then connected to monitoring equipment to allow obtaining EEG data from the patient.

During an EEG recording session, the patient may require detachment of the connector assembly 14, for example, to take a shower. When this is required the patient grips the connector assembly 14 and withdraws the locating protrusions 76 from the locating apertures 54 by exerting a force greater than the force due to magnetic attraction between the magnets 50, 62. The patient can subsequently re-attach the connector assembly 14 as discussed above. The self-aligning characteristic of the magnets 56, 62 can be particularly useful in this scenario as the carrier assembly 12 may be installed out of sight, such as at a rear of the scalp.

The disclosed assembly 10 has a carrier assembly 12 carrying an electrode 18 array which is releasably connectable to a connector assembly 14. Connecting the assemblies 12, 14 involves engaging complementary location formations 32 which allows complementary retention features 30 to secure the assemblies 12, 14 together, forming a mechanical and electrical engagement simultaneously. This readily allows connection and disconnection of an EEG array to monitoring equipment. This usefully enhances patient comfort, hygiene and well-being. Furthermore, this allows clinicians to install the assembly 10 quickly, enhancing efficiency of medical staff.

During installation of the carrier assembly 12 to the patient, a clinician can readily adjust the length of wires 34 between the assembly 12 and the electrodes 18 to ensure a taught fit, and retain the wires 34 in position, with the first housing 22, to maintain the fit. This advantageously improves patient comfort. This also allows the carrier assembly 12 to be arranged on top of a patient's head which reduces likelihood of the carrier assembly 12 colliding with other objects during use, for example, whilst the patient is sleeping. This also avoids requiring differently sized carrier assemblies 12 for differently sized patients.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An electrode array assembly including:

a carrier assembly including an array of first electrical contacts coupled to a plurality of electrodes, and a first housing carrying the array of first contacts and configured to allow access to the first contacts; and a connector assembly including an array of second electrical contacts and a second housing carrying the array of second contacts and configured to allow access to the second contacts, wherein each of the carrier assembly and the connector assembly include complementary retention elements and complementary locating formations, whereby engaging the complementary locating formations allows the complementary retention elements to secure the first housing to the second housing, and allows the first contacts to couple with the second contacts, wherein the retention element of the carrier assembly includes at least one first magnetic element enclosed in the first housing, and the retention element of the carrier assembly includes at least one second magnetic element enclosed in the second housing, and wherein the, or each, second magnetic element is arranged to be drawn towards the, or each, first magnetic element when the locating formations are engaged.

2. The assembly of claim 1, wherein the locating formation of the carrier assembly includes at least one locating aperture defined by the first housing, and the locating formation of the connector assembly includes at least one locating protrusion defined by the second housing, and wherein the, or each, locating protrusion is dimensioned to be at least partially received in the at least one locating aperture.

3. The assembly of claim 2, wherein the first housing defines a plurality of the locating apertures arranged in a circular array around the first contacts, and the second housing defines a complementary plurality of the locating protrusions arranged in a circular array around the second contacts.

4. The assembly of claim 3, wherein each of the locating protrusions defines a tapered free end shaped to allow guiding the protrusion into one of the locating apertures.

5. The assembly of claim 1, wherein each of the at least one first magnetic element and the at least one second magnetic element is configured as a ring magnet and arranged to surround the respective contacts.

6. The assembly of claim 1, wherein the first contacts are configured as pads, and the second contacts are configured as pins.

7. The assembly of claim 6, wherein the first housing defines an array of contact apertures, each contact aperture arranged to allow access to one of the pads.

8. The assembly of claim 1, wherein each of the electrodes are coupled to one of the first contacts by a wire, and wherein the first housing includes a base plate defining a plurality of openings, each opening dimensioned to receive one of the wires.

9. The assembly of claim 8, wherein the first housing further includes a cover securable to the base plate to retain the wires in the openings.

10. The assembly of claim 9, wherein the cover defines a rib extending at least partially around a peripheral region, the rib arranged so that securing the cover to the base plate clamps the wires between the base plate and the rib.

11. An electrode array assembly including:

a plurality of electrodes coupled to a respective plurality of wires;

a base plate configured to carry the plurality of electrodes and wires, and defining a plurality of openings, each opening dimensioned to receive one of the wires; and a first cover securable to the base plate to retain the wires in the openings.

12. The assembly of claim 11, wherein the first cover defines a rib extending at least partially around a peripheral region, the rib arranged so that securing the first cover to the base plate clamps the wires between the base plate and the rib.

13. The assembly of claim 11, further including an array of electrical contacts coupled to the plurality of electrodes, and a second cover securable to the base plate to cover the electrical contacts, the second cover defining a plurality of apertures configured to allow access to the electrical contacts.

14. An electrode array assembly including:

a carrier assembly including an array of first electrical contacts coupled to a plurality of electrodes, and a first housing carrying the array of first contacts and configured to allow access to the first contacts; and a connector assembly including an array of second electrical contacts and a second housing carrying the array of second contacts and configured to allow access to the second contacts, wherein each of the carrier assembly and the connector assembly include complementary retention elements and complementary locating formations, whereby engaging the complementary locating formations allows the complementary retention elements to secure the first housing to the second housing, and allows the first contacts to couple with the second contacts, wherein each of the at least one first magnetic element and the at least one second magnetic element is configured as a ring magnet and arranged to surround the respective contacts.

15. The assembly of claim 14, wherein the locating formation of the carrier assembly includes at least one locating aperture defined by the first housing, and the locating formation of the connector assembly includes at least one locating protrusion defined by the second housing, and wherein the, or each, locating protrusion is dimensioned to be at least partially received in the at least one locating aperture.

16. The assembly of claim 15, wherein the first housing defines a plurality of the locating apertures arranged in a circular array around the first contacts, and wherein the second housing defines a complementary plurality of the locating protrusions arranged in a circular array around the second contacts.

17. The assembly of claim 16, wherein each of the locating protrusions defines a tapered free end shaped to allow guiding the protrusion into one of the locating apertures.

18. The assembly of claim 14, wherein the first contacts are configured as pads, and wherein the second contacts are configured as pins.

19. The assembly of claim 14, wherein each of the electrodes are coupled to one of the first contacts by a wire, and wherein the first housing includes a base plate defining a plurality of openings, each opening dimensioned to receive one of the wires.

20. The assembly of claim 14, wherein each of the electrodes are coupled to one of the first contacts by a wire, and wherein the first housing includes a base plate defining a plurality of openings, each opening dimensioned to receive one of the wires.

* * * * *